(12) United States Patent
Yamamoto et al.

(10) Patent No.: US 6,690,975 B2
(45) Date of Patent: Feb. 10, 2004

(54) METHODS FOR TREATING HEPATITIS C

(75) Inventors: Itsuo Yamamoto, 17-10, Tsutsumimachi 3-chome, Yao-shi, Osaka (JP); Iwao Nishide, 236, Kaizuka, Kaizuka-shi, Osaka (JP); Susumu Yukawa, 840-1, Musotani, Wakayama-shi, Wakayama (JP); Ostapenko Valentyna, 14-5-201, Hori 1-chome, Kaizuka-shi, Osaka (JP)

(73) Assignees: Bistner Co., Ltd., Tokyo (JP); Iryodenshiseiko Co., Ltd., Osaka (JP); Yamamoto Vinita Co., Ltd., Osaka (JP); Itsuo Yamamoto, Osaka (JP); Iwao Nishide, Osaka (JP); Susumu Yukawa, Osaka (JP); Ostapenko Valentyna, Osaka (JP)

( * ) Notice: Subject to any disclaimer, the term of this patent is extended or adjusted under 35 U.S.C. 154(b) by 26 days.

(21) Appl. No.: 10/151,218

(22) Filed: May 17, 2002

(65) Prior Publication Data

US 2003/0216798 A1 Nov. 20, 2003

(51) Int. Cl.[7] .................................................. A61F 2/00
(52) U.S. Cl. .......................... 607/101; 607/154; 607/99
(58) Field of Search ............................. 607/96, 98, 99, 607/101, 102, 154; 128/898

(56) References Cited

U.S. PATENT DOCUMENTS 6,326,151 B1 * 12/2001 Katze et al. .................... 435/6
6,347,633 B1 * 2/2002 Groth et al. ................ 128/898
6,402,689 B1 * 6/2002 Scarantino et al. ......... 600/300

OTHER PUBLICATIONS

Hyperthermia Treatment System for Cancer Therapy Thermotron–RF8 Published by Yamamoto Vinita Co., Ltd.— May 1, 2001.

* cited by examiner

Primary Examiner—Roy D. Gibson
(74) Attorney, Agent, or Firm—Anthony J. Casella; Gerald E. Hespos

(57) ABSTRACT

While an interferon therapy is a conventional method for treating hepatitis C, no particular option exists currently in the treatment except for this interferon therapy. An object of the present invention is to provide a novel method for treating hepatitis C. The present invention includes a method for treating hepatitis C comprising warming a liver region of a human by sandwiching an upper abdominal region of a human body between electrodes on the front and back by supplying a high-frequency electric power to these electrodes.

16 Claims, 10 Drawing Sheets

METHODS FOR TREATING HEPATITIS C

BACKGROUND OF THE INVENTION

1. Field of the Invention

The present invention relates to a method for treating hepatitis C, which is effective even in the case of severe chronic hepatitis C.

2. Description of the Prior Art

Hepatitis C is infectious disease caused by the Hepatitis C virus (HCV). The proliferation of HCV in liver is the cause of the onset of this disease, and after the onset HCV spread to the blood.

An interferon therapy is believed to be the only one practically effective method for treating hepatitis C, the interferon is administered alone or with other pharmaceuticals.

A treatment with an interferon involves, depending on the severity of a particular case, an interferon injection once a day for 4 weeks followed by once per two days for 22 weeks while observing any change in the condition. In the case where no improvement is observed even after such an interferon therapy being continued over a half year (one therapeutic term is a half year), the interferon therapy may be continued similarly further for a half year.

While it is highly desired to accomplish a complete recovery from hepatitis C, especially from chronic hepatitis C, which may lead to hepatic cirrhosis or cancer when being allowed to be left as it is, a severe case which missed the chance of the complete recovery and allowed the disease to be a chronic or grave one, such as a case classified as "lb", can not expected to be treated successfully with any interferon therapy. As one of the indices of hepatitis C, the blood hepatitis C virus-derived RNA level (hereinafter sometimes referred to as HCV RNA) is known, and a case whose HCV RNA level before an interferon therapy is about 100 k copies can be expected to be treated successfully with the interferon, but a case whose HCV RNA level is 200 to 300 k copies or more is believed to exhibit a poor therapeutic effect.

On the other hand, an interferon therapy may have side effects such as the onset of a thyroidal disease or fever, retinopathy, depression and the like, and a repetitive interferon therapy may be an extreme burden not only economically but also physically and mentally due to these side effects especially in a case where no therapeutic effect is expected.

SUMMARY OF THE INVENTION

The invention is a method for treating hepatitis C, and intended to ameliorate the symptoms of hepatitis C or to accomplish a recovery therefrom by means of warming a liver region of a human.

DESCRIPTION OF THE PREFERRED EMBODIMENTS

Figure 1:
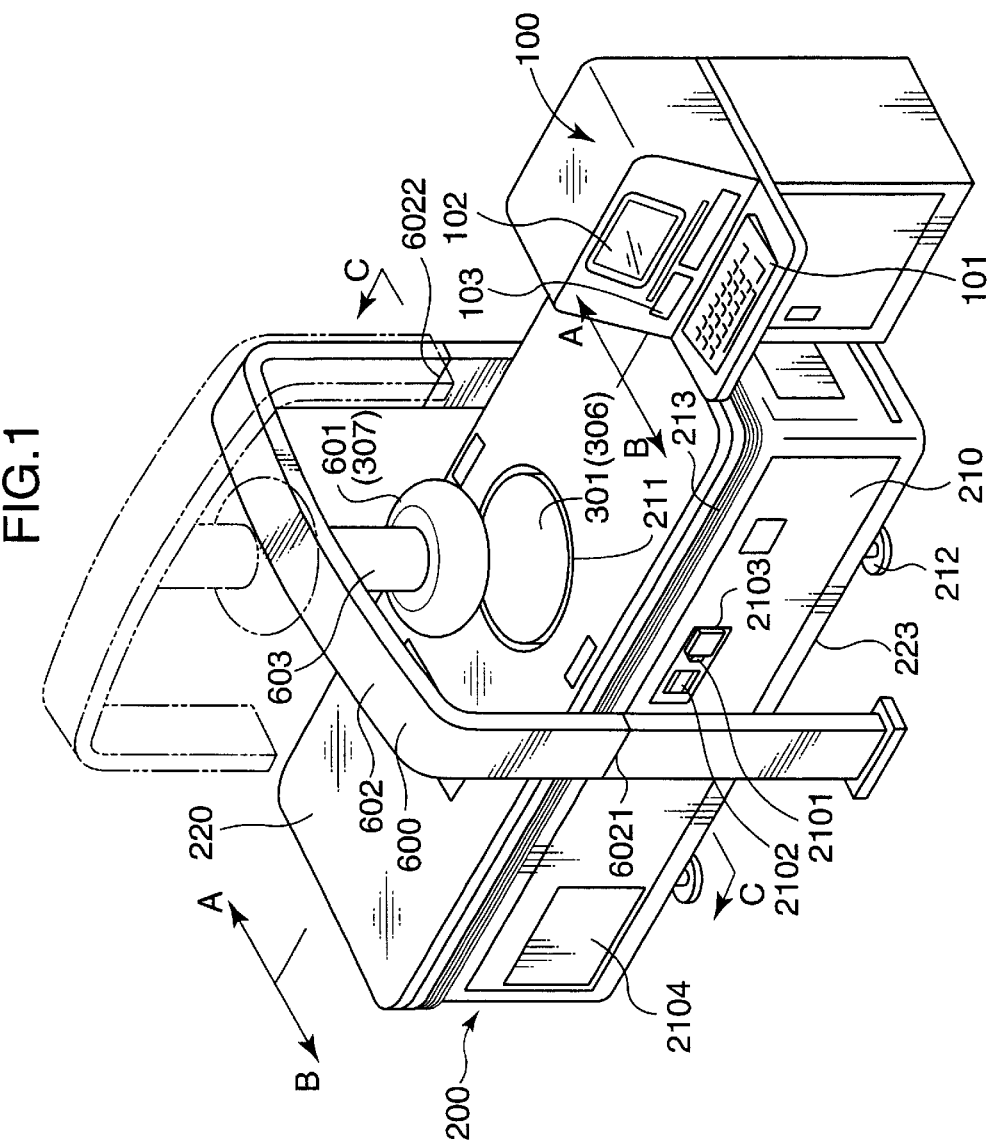
FIG. 1 shows a perspective view of one embodiment of the present inventive high-frequency warming therapeutic device.

An aspect of a method for treating hepatitis C according to the present invention is to warm a liver region of a human body at 39 to 42° C. by supplying a high-frequency electric power.

A recommended highly effective means for warming to a temperature specified above involves sandwiching an upper abdominal region of a human body between electrodes on the front and back by supplying a high-frequency electric power to heat a targeted lesion. In this procedure, the supplied electric power is preferably within the range from 200 to 1500 W. The upper abdominal region of a human body may be warmed while being sandwiched by the electrodes described above on the sides.

Alternatively, an aspect of a method for treating hepatitis C according to the present invention involves sandwiching the upper abdominal region of a human body between electrodes on the front and back by supplying a high-frequency electric power of 200 to 1500 W to the electrodes, without controlling the temperature as specified above.

While it has already been established in clinical studies targeting a large number of patients that the warming of the liver region as described above exhibits a satisfactory therapeutic effect on hepatitis C, the reason for such therapeutic effects observed practically may be considered as follows. Thus, it is possible that a warming of the liver by supplying a high-frequency leads locally to an increased immune activity and additionally an apotosis of the infected cells. For further information, it is to be thought as functional mechanism that warming by supplying a high-frequency activate the natural immunity such as Kupffer cells, dendritic cells, macrophages, NK cells, leukocyte, interferon, or the like, and thus, inactivate nonspecifically hepatitis C virus and infected cells and the infection by them to non-infected cells around infected cells is prevented. And antigen presenting is carried out by the natural immunity mentioned above and activates acquired immunity by cytokine, lymphokine, chemokine, or the like. Moreover, the warming by supplying a high-frequency mentioned above activates humoral immunity such as antibody and so on or cell-mediated immunity in the acquired immunity. It is to be thought that hepatitis C virus are inactivated by this antibody and the cells infected by hepatitis C virus antigenic-specifically meet their death (apotosis) by the activated cytoxic T lymphocytes (CLT) or the like. Thus, the warming by supplying a high-frequency stimulates the production of the interferon and have an effect on treatment by generally influencing immune system.

A method for warming the liver region by supplying an electric power described above may be a method for warming the liver region by supplying a high-frequency electric power for example at 8 MHz onto the surface of a human body using a high-frequency warming medical device.

Also in the present invention, it is preferred to supply the electric power described above for a period of 30 to 60 minutes each time, which allows the liver region to be warmed sufficiently, whereby obtaining an enhanced therapeutic effect each time.

In addition, it is also preferred in the present invention to supply the electric power, for example, once a week or more (preferably, two or three times a week), and 15 times or more in total, since a repetitive and cumulative operation 15 times or more is desired in order to exert the therapeutic effect of the warming described above sufficiently.

It is also preferred to perform the operation consecutively to some extent, for example, one time every day or every other day over a period from Monday through Friday a week as a unit period. Such a consecutive therapy allows the immune activity to be enhanced continuously, whereby preventing any reduction in the therapeutic effect due to a reduction in the immune activity attributable to the intermission of the therapy. Thus, the therapeutic effect is increased by performing the operation everyday or every other day rather than performing at a certain interval such as three days. Nevertheless, the warming treatment at an interval of more days may be acceptable in some patients.

It is also preferred in the present invention to supply the electric power described above while taking the systemic condition and the hepatitis C indices (for example, HCV RNA) of a patient into consideration. Thus, the therapeutic method may vary depend on the condition of the patient to avoid any burden to the patient.

Also in the present invention, it is also possible to administer an interferon concomitantly while taking the systemic condition and the hepatitis C indices (for example, HCV RNA) of a patient into consideration. The interferon may be administered for example by injecting it once a day every day for 4 weeks and then every other day for 22 weeks, as is administered conventionally.

While the warming of the liver region described above mainly gives an increased immune activity which then reduces the hepatitis C virus-producing ability whereby enhancing the therapeutic effect, the concomitant use of an interferon as described above serves to give a further enhanced therapeutic effect. Especially in a case where the warming treatment reduced the HCV RNA level to about 100 k copies, a high therapeutic effect of the interferon therapy can also be expected.

In addition, the present inventive method may be switched into an interferon therapy while taking the systemic condition and the hepatitis C indices (for example, HCV RNA) of a patient into consideration. Exemplified methods of the therapy include (1) the warming therapy over a certain period followed by switching into an interferon therapy, (2) the warming therapy over a certain period followed by a concomitant therapy with an interferon therapy for a certain period followed by switching into an interferon therapy alone, (3) the warming therapy concomitantly with an interferon therapy for a certain period followed by switching into an interferon therapy alone, or the like.

It is also preferred in the present invention to measure the impedance between the both electrodes described above based on which a certain percentage change (for example 10% although it may vary depend on the patient) is selected as a target, the attainment of which gives a feedback to control the electric power. Such a control of the electric power is required since an impedance value is indicative of the temperature of the liver region and a departure from the range of the targeted percentage change specified above (for example 10%) may pose a risk of an excessive warming of a human body.

High-frequency warming therapeutic device

A high-frequency supplier (high-frequency warming therapeutic device) employed in a method for treating hepatitis C according to the present invention is described below.

Figure 2:
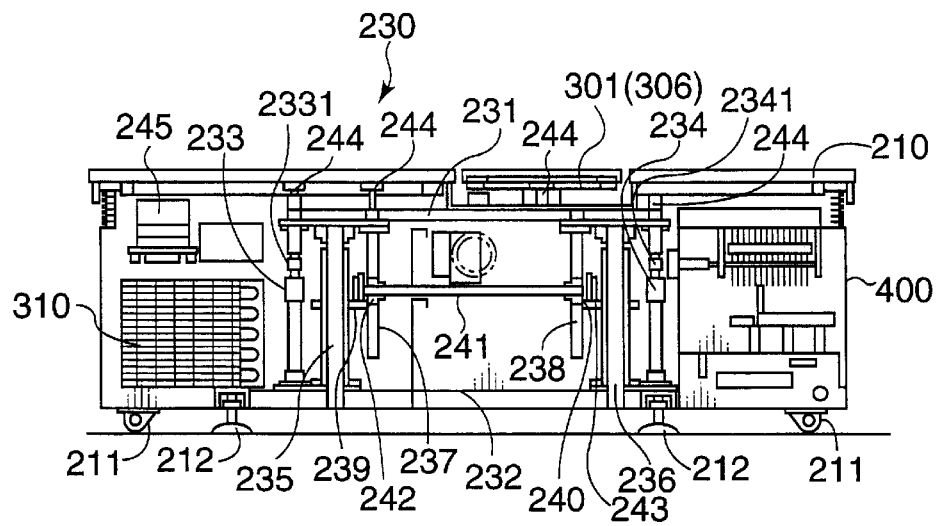
FIG. 2 shows the A—A sectional view of FIG. 1.
Figure 3:
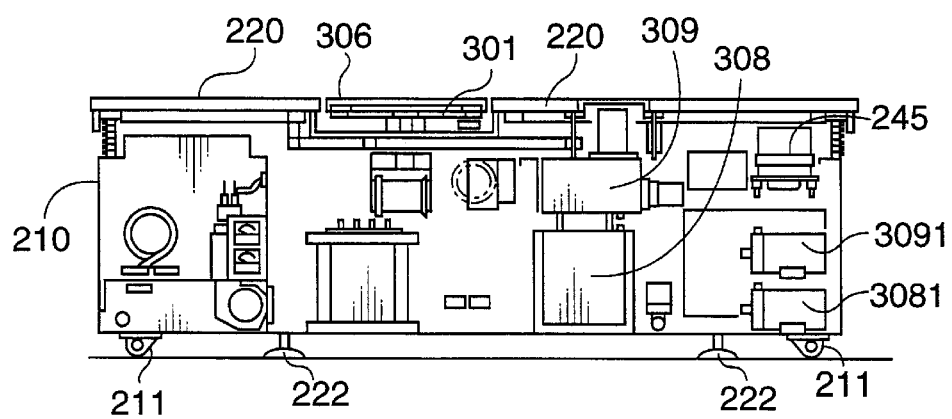
FIG. 3 shows the B—B sectional view of FIG. 1.
Figure 4:
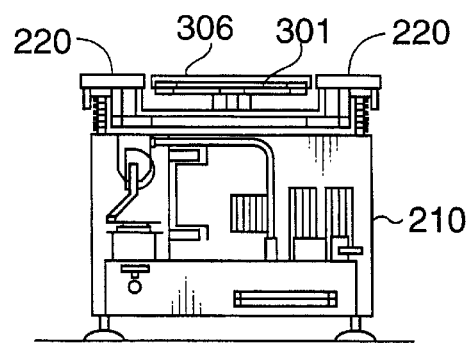
FIG. 4 shows the C—C sectional view of FIG. 1.

FIG. 1 shows a perspective view of one embodiment of the high-frequency warming therapeutic device of the present inventive. FIG. 2 shows the A—A sectional view of FIG. 1, FIG. 3 shows the B—B sectional view of FIG. 1, and FIG. 4 shows a operation bed body 200 as the sectional view of C—C indicated in FIG. 1. This high-frequency warming therapeutic device is provided with a controller 100, the operation bed body 200 and a upper electrode unit 600 as fundamental components, and the operation bed body 200 is provided with a lower electrode 301.

The controller 100 contains a desktop console having a operating device 101 on the central rack, a display 102 and a data output 103 such as a printer in the upper position, and in the lower position a controller circuit is enclosed. The operating device 101 serves to control the high-frequency warming therapeutic device, and is provided with a keyboard for inputting a command etc. The display 102 serves to monitor the condition of a patient being operated, and also to indicate various data. The data output 103 serves to output the patient data as appropriate.

The operation bed body 200 is provided with a housing 210 the upper side of which has an opening and a table 220, which cover the upside of the housing and is large enough to receive a patient being lying down, and the housing 210 encloses a high-frequency generator and other components.

The Bottom of housing 210 is provided with wheels 211 at the four corners as shown in FIG. 2 for the purpose of moving the operation bed body 200 easily, and fixing a components 212 for fixing the operation bed body 200 in a certain position are provided preferably in well-balanced 4 positions on an identical plane. Each fixing component 212 is in the form for example of a screw engagement structure, which allows it to be raised or lowered relative to the operation bed body 200 in response to the rotation of the screw although the character is not shown in the Figure.

The operation bed body 200 has its controller 100 on the side of the head of a patient, whereby allowing a physician to interview the patient readily while watching the display 102. Accordingly, the following description is based on the condition in which the head is placed in the right side in FIG. 1 and the legs are placed in the opposite side, and the left half of the body when viewed from the head (the side indicated on the display 102) is placed in front.

The housing 210 is provided with a main switch 2101 in the center front which turns the power of the high-frequency warming therapeutic device on and off, in a position close to which a voltage meter 2102 and a current meter 2103 are provided, together with openings of appropriate sizes for releasing heat etc fitted with a mesh cover 2104 in appropriate positions including the front The upper electrode unit 600 is provided with a discshaped upper electrode 601 which is supported by a arch 602, and upper electrode 601 is connected to the arch 602 via a arm 603. The length of the arm 603 can be changed, and shortened by 15 cm at maximum by depressing. One leg of the arch 602 can be separated at a separation point 6021, and the other leg is allowed to rotate at a rotation point 6022. Accordingly, by separating at the separation point 6021 and rotating the arch 602 around the rotation point 6022 as a rotation axis, the upper electrode 601 can be released from the top of the table 220 as shown by the two dot-intermitted line in FIG. 1.

The lower electrode 301 mentioned above fitted to the operation bed body 200 is in the shape of a disc, which is engaged coplanarly with a round opening 221 formed in a position which is somewhat closer to the head than the center of the table 220. The lower electrode 301 and the upper electrode 601 mentioned above sandwich an upper abdominal region of a lying patient in such a manner that the liver of the patient can be positioned stably between facing electrodes consisting of the lower electrode 301 and the upper electrode 601. The upper electrode 601 is connected electrically via the arch 602 to the lower electrode 301, and the upper electrode 601 is earthed. By forming an earth potential space by the arch 602 around the lower electrode 301 and the upper electrode 601, the divergence of electrodynamic lines from the lower electrode 301 toward the ground is prevented, whereby ensuring a uniform electric field distribution between the facing electrodes. On the surfaces of the facing sides of the lower electrode 301 and the upper electrode 601, cooling pads 306 and 307 are bonded. These cooling pads 306 and 307 are connected with a water pipe.

The housing 210 contains a high-frequency generator 400 on the head side which generates a predetermined high-frequency electric power, a up-down mechanism 230 which raises or lowers the table 220, a cool water tank 308 and a warm water tank 309 on the leg side. The cool water tank 308 enables the supply and circulation of water at room temperature into cooling pads 306 and 307 via a water pipe and a chiller 310 (see FIG. 2), while the warm water tank 309 enables the supply and circulation of water at about a body temperature into cooling pads 306 and 307, the both being fitted with water pumps 3081 and 3091. By merging the water pipes halfway and providing each upstream with a one-way valve, the exchange between the warm and cool waters can be accomplished only by switching the drive between the cool water pump and the warm water pump. At the beginning of the heating of a target lesion, warm water at about a body temperature is supplied to cooling pads 306 and 307. For the purpose of avoiding an elevated body temperature after the heating for a certain period, cool water is supplied to cooling pads 306 and 307.

The Up-down mechanism 230 consists of a cylinder substrate 232 provided on the bottom of the housing 210, hydraulic cylinders 233 and 244 mounted on two sites in the cylinder substrate 232 and a up-down plate 231 on the upper side (thus enabling an up-down movement over 15 cm at maximum). The up-down mechanism 230 is provided also with a horizontally-maintaining mechanism capable of moving up-down plate 231 as being kept horizontal. The horizontally-maintaining mechanism consists of guides 235 and 236 mounted on two sites in the bottom of the housing 210, racks 237 and 238 connected with the back side of the up-down plate 231 downward in two positions, a connecting arm provided with pinions 239 and 240 on its both sides and connected to racks 237 and 238 via pinions 239 and 240, and fixing components 242 and 243 capable of fixing a connecting arm 241 rotatably in an almost central position between guides 235 and 236.

The connecting arm 241 serves to enable a synchronized up-down movement to ensure the same vertical positions between piston rods 2331 and 2341. Even under an identical hydraulic pressure of both hydraulic cylinders 233 and 234, the difference in the load between hydraulic cylinders when a patient is lying down may lead to a slight difference in the vertical position between piston rods 2331 and 2341 which may result in a difficulty in moving the up-down plate 231 as being horizontal. Accordingly, the movement of piston rods 2331 and 2341 with keeping their vertical positions identical is ensured by means of the connecting arm 241.

In several appropriate points on the upper side of the up-down plate 231 over which a load can uniformly be distributed, for example 6 points in total including 4 corners of the up-down plate 231 and two points located laterally in the widthwise direction and somewhat closer to the legs than the center, a connecting components 245 are mounted, the upper end of components 245 is attached to the table 220. Also on the site corresponding to the center of the round opening 221 in the up-down plate 231, the connecting component 245 is mounted, whereby supporting and attaching to the lower electrode 301. A universal joint is provided at the point of the attachment of the lower electrode 301 with the connecting component 245, whereby allowing only the lower electrode 301 to be moved up and down. By placing the lower electrode 301 higher than the table 220, a close contact between the table 220 and the legs is ensured.

The hydraulic unit 245 is a known unit, which is provided with a pump capable of supplying an oil stored in an oil tank to hydraulic cylinders 233 and 234 under a certain pressure and also provided with a hydraulic valve, and serves to adjust the height of the table 220 by driving the pump.

The up-down plate 231 can be kept horizontal as described below: pinions 239 and 240 rotate when racks 237 and 238 are elevated by up-down plate 231, resulting in the rotation of the connecting arm 241. This rotation of the connecting arm 241 enables a synchronized movement of both piston rods 2331 and 2341. Accordingly, the up-down plate 231 can be moved up and down while being kept horizontal.

Figure 5:
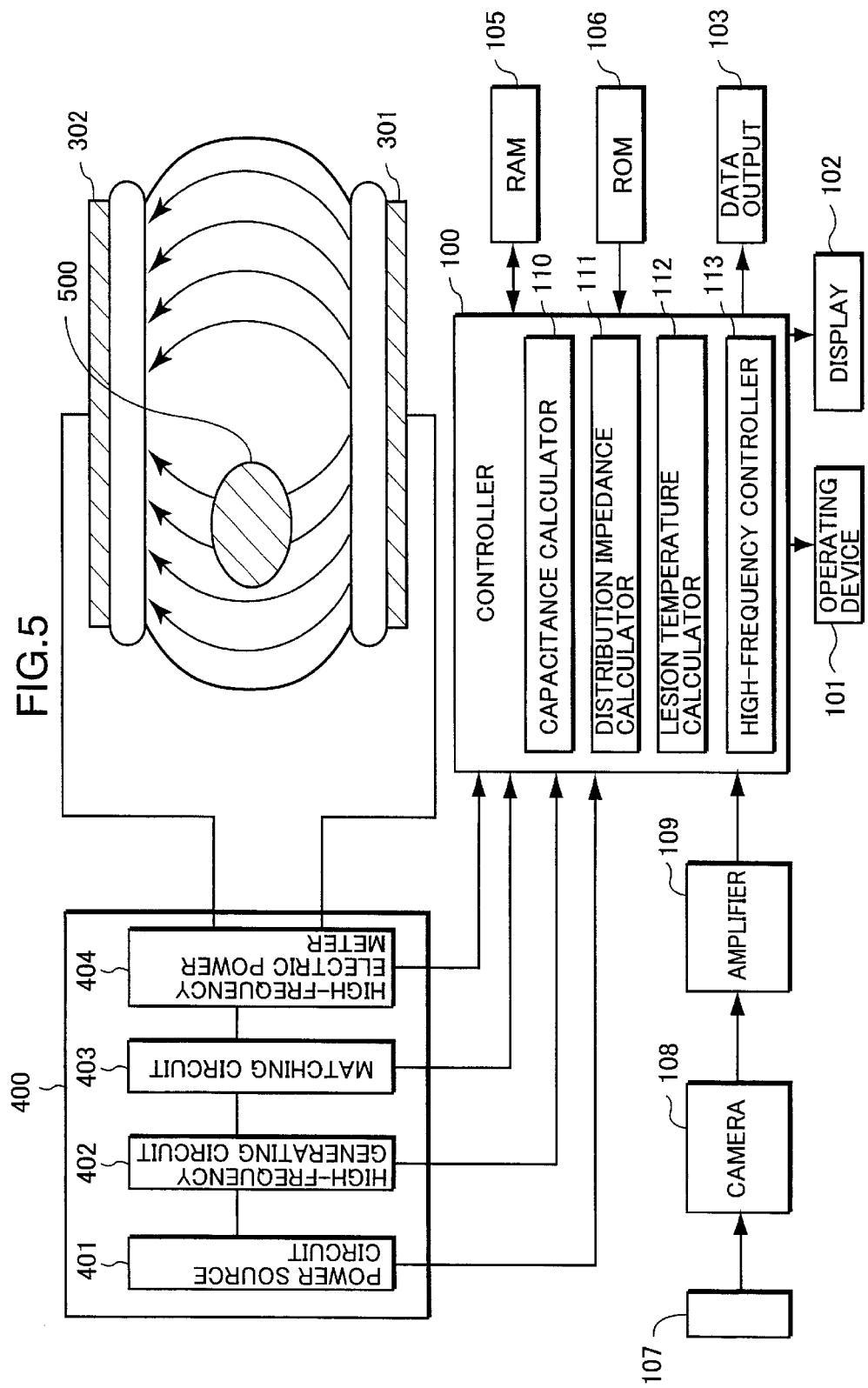
FIG. 5 shows a block diagram of the high-frequency warming therapeutic device.

FIG. 5 shows a block diagram of a high-frequency warming therapeutic device of the embodiment.

A high-frequency generator 400 is provided with a power source circuit 401, a high-frequency generating circuit 402, a matching circuit 403 and a high-frequency electric power meter 404. The power source circuit 401 supplies a certain level of electric power to the high-frequency generating circuit 402. The high-frequency generating circuit 402 generates a high-frequency electric power of about 1 KW for example at 8 MHz in a self-exciting oscillation mode. The high-frequency electric power meter 404 measures a high-frequency electric power supplied to the facing electrodes. The high-frequency electric power meter 404 detects an incident power to and a reflected power from the facing electrodes or determines the supplied power to the load based on the output power and the incident power. A value measured by the high-frequency electric power meter 404 is input to the controller 100 and displayed on the display 102.

The matching circuit 403 according to this embodiment consists of a variable condenser, whose capacitance is adjusted to alter the output impedance, whereby accomplishing an impedance consistency between the high-frequency generating circuit 402 and an object between the facing electrodes, i.e., a load. The controller 100 can know the capacitance component of the load based on the level adjusted for the condenser.

Tomographic picture 107 is an X-ray image obtained by a CT (computer tomography) scanner or a photograph of a living tissue obtained by an MRI (magnetic resonance imaging). The intensity of the image corresponds to the density of the sectional area including target lesion 500.

A camera 108 consists of an area sensor and so on in which CCDs (charge-coupled device) are aligned, and serves to take the tomographic picture 107 including the target lesion of a patient. An image signal thus taken is then converted into an electric signal, conducted into the controller 100 via an amplifier 109, and recorded as intensity data D (i,j) in a RAM 105. The designation (i,j) shown here indicates the address in the RAM corresponding to the respective position in the sectional area, and the intensity has a certain bit number suitable for the arithmetic accuracy described below and is represented for example by a 8-bit tone.

When the intensity data D (i,j) are transmitted for example by a communicative means or from any external memory, they may be received by an interface instead of the camera 108.

A ROM 106 stores programs and arithmetic equations or tables to execute various functions of the controller 100 as well as various data required to be processed. The ROM 106 stores initial capacitance component CO of the load, electric field distribution model K (i,j) obtained from the shape of and the distance between the facing electrodes, and initial distribution impedance ρ0 (i,j) at the respective point in the sectional area of target lesion 500. Electric field distribution model K (i,j) and initial distribution impedance ρ0 (i,j) may be those obtained by a calculation based on the distance between the facing electrodes and a previous simulation conducted using a uniform dielectric subject sandwiched therein.

The Controller 100 consists of a capacitance calculator 110 which calculates a capacitance component C of the load from the level adjusted for a variable condenser of the matching circuit 403, a distribution impedance calculator 111 which calculates a distribution impedance change Δρ (i,j) at the respective point in the sectional area of target lesion 500 by Equation 2 described later, a lesion temperature calculator 112 which calculates a temperature distribution change ΔT (i,j) at the respective point in the sectional area of target lesion 500 and the high-frequency controller 113 which controls an output power from the high-frequency generating circuit 402.

The capacitance calculator 110 calculates a capacitance component C between the facing electrodes which varies depending on the change in the temperature of the body sandwiched between the facing electrodes based on the level adjusted for a variable condenser of the matching circuit 403.

The distribution impedance calculator 111 calculates the distribution impedance ρ (i,j) corresponding to the point (i,j) in the sectional area of target lesion 500 predetermined via operating device 101 based on the initial distribution impedance ρ0 (i,j) and the distribution impedance change Δρ (i,j). The distribution impedance calculator 111 calculates the distribution impedance change Δρ (i,j) as described below. A change ΔF (i,j) in F (i,j) after supplying a high-frequency for a certain period is calculated in accordance with Equation 1.

$$\Delta F(ij) = \alpha \times (C - CO) \times D(ij) \times K(ij)$$  EQUATION 1

C: Measured capacitance between facing electrode
CO: Initial capacitance between facing electrode
D (i,j): Intensity of tomographic picture
K (i,j): Electric field distribution model between facing electrodes
α: Coefficient The impedance of the load here can be represented as $1/2\pi fC$ assuming that the inductance and resistance components are negligibly small when compared with the conductance component. Accordingly, by utilizing this formula $1/2\pi fC$, the distribution impedance change Δρ (i,j) after initiation of the high-frequency supply can be calculated in accordance with Equation 2.

EQUATION 2

$$\Delta \beta(ij) = \frac{\alpha}{2\pi f(C - CO) \times D(ij) \times K(ij)}$$

The distribution impedance change Δρ (i,j) thus calculated appears as a graph on the display 102.

Figure 6:
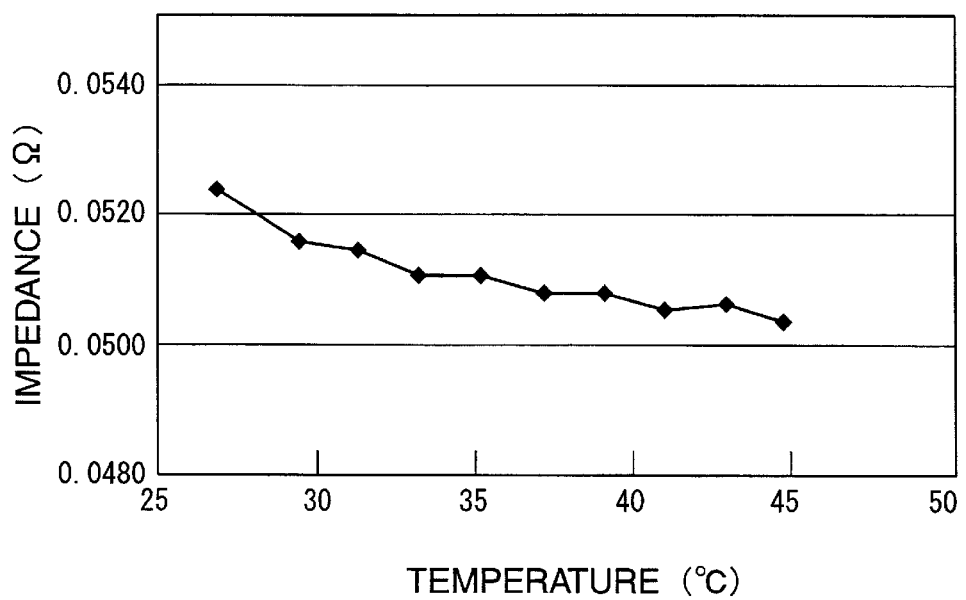
FIG. 6 shows the graph indicating the relationship between the attained temperature of the lesion subjected to the high-frequency warming therapy and the load impedance.

FIG. 6 shows the graph indicating the relationship between the attained temperature of the lesion subjected to the high-frequency warming therapy and the load impedance. Since there is a correlation between the load impedance and the temperature as evident from FIG. 6, there can also be a correlation between the distribution impedance change Δρ (i,j) and the distribution temperature T (i,j) as shown in FIG. 6. Based on this correlation, the value of the distribution temperature T (i,j) is determined directly from the value of the distribution impedance ρ (i,j).

The lesion temperature calculator 112 calculates a temperature distribution change ΔT (i,j) from a distribution impedance change Δρ (i,j) calculated by the distribution impedance calculator 111 based on the correlation between the distribution impedance ρ (i,j) and the distribution temperature T (i,j) as shown in FIG. 6. The ROM 106 stores the relationship between the distribution impedance change Δρ (i,j) and the temperature distribution change ΔT (i,j) in a table format. The lesion temperature calculator 112 reads the temperature distribution change ΔT (i,j) out of the distribution impedance change Δρ (i,j) with referring to the ROM 106. The temperature distribution change ΔT (i,j) calculated by the lesion temperature calculator 112 appears as a graph on the axis of the time.

The high-frequency controller 113 controls the high-frequency electric power level as an output from the high-frequency generator 400 in order to keep the distribution impedance change Δρ (i,j) at a certain level or controls the power supply intermittently. The distribution impedance ρ (i,j) in target lesion 500 can be obtained by adding the distribution impedance change Δρ (i,j) to the initial distribution impedance ρ0 (i,j). Accordingly, a target value of the distribution impedance ρ (i,j) can be obtained by converting the capacitance component C of the load into a value corresponding to the target value of the distribution impedance ρ (i,j) by Equation 2, whereby allowing the distribution impedance ρ (i,j) to be handled as a control component. The ROM 106 stores an output power from the high-frequency generating circuit 402 as being related to the distribution impedance ρ (i,j). Once a target distribution impedance is determined, the high-frequency controller 113 reads an output power level of the high-frequency generating circuit 402 corresponding to the target distribution impedance out of the ROM 106 to determine the output power level of the high-frequency generating circuit 402, whereby controlling high-frequency generating circuit 402.

In addition to the control of the high-frequency supply is controlled based on the distribution impedance change Δρ (i,j) as in the embodiment described above, the control based on the temperature distribution change ΔT (i,j) is also possible.

Method for Warming Human Liver Region

A method for warming the human liver region using a high-frequency warming therapeutic device described above is described below.

Figure 7:
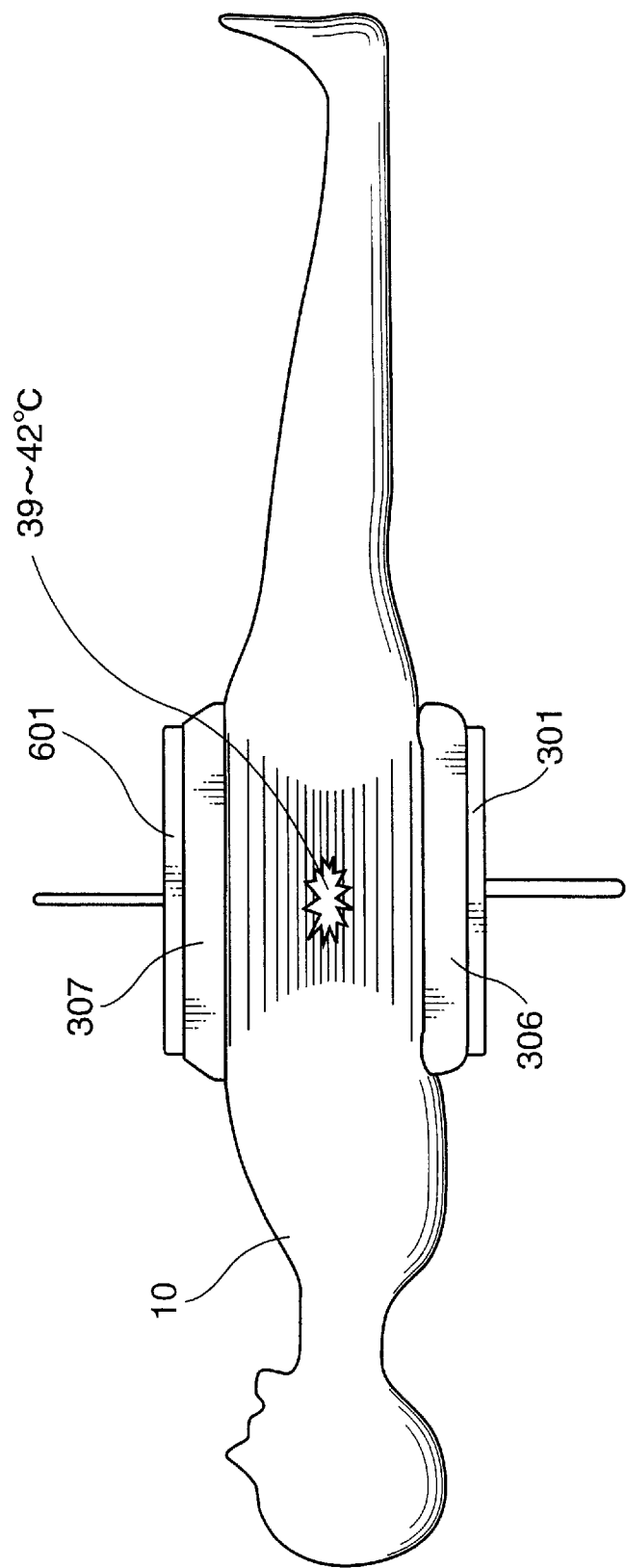
FIG. 7 shows an outline of the side view of the high-frequency warming therapeutic device whose electrodes sandwich an upper abdominal region of a patient.

The upper electrode 601 and the arch 602 have previously been removed from the top of the table 220 (see the two dot-intermitted line in FIG. 1), and a patient 10 lies down on the top of the table 220. Rotating the arch 602 is allowed to rotate around the rotation point 6022 as an axis to establish an attachment at the separation point 6021 (see the solid line in FIG. 1) while positioning the upper electrode 601 above the upper abdominal region of the patient 10. Then, the up-down mechanism 230 is driven to raise the table 220 and the patient is sandwiched between the upper electrode 601 and the lower electrode 301 at the front and the back. By sandwiching the upper abdominal region between electrodes 601 and 301, the liver of the patient is located between the upper electrode 601 and the lower electrode 301. FIG. 7 shows an outline of the side view of the high-frequency warming therapeutic device whose electrodes 601 and 301 sandwich the upper abdominal region of the patient 10.

Subsequently, a high-frequency electric power (for example 1000 to 1500 W at 8 MHz) is supplied to the upper electrode 601 and the lower electrode 301 to warm the liver region of the patient at 39 to 42° C. (preferably 40 to 41° C.). This power supply is continued for 30 to 60 minutes, whereby completing a single warming treatment. During the power supply described above, it is preferable to avoid any excessive warming of the human body surface by supplying cool water as appropriate to cooling pads 306 and 307.

A warming treatment by the electric supply as described above is performed for example once a day, three times or more a week and 15 times or more in total. Alternatively, the warming treatment by the electric supply is performed for example once a day five to 6 times a week for two weeks followed by the subsequent two weeks during which the warming treatment by the electric supply as described above is performed twice a week concomitantly with an interferon injection once a day 6 times a week for two weeks. Such a concomitant therapy involving the warming treatment by the electric supply as described above together with the interferon therapy is expected to exhibit a further higher therapeutic effect.

In addition to the therapeutic modes described above, various other modes may be employed, for example warming treatment by the electric supply as described above is performed for example once a day 5 times or more continuously (5 days or longer).

Trial 1

A trail of an inventive treatment in hepatitis C patients (case Nos.1 to 5) is described below.

All of Case Nos.1 to 5 were chronic hepatitis C patients whose hepatitis C levels are 1b, and almost no therapeutic effects were noted especially in Case Nos.1 to 4 in spite of the treatment with interferon over 2 therapeutic terms (one therapeutic term is a half year). The high-frequency warming therapeutic device employed here had the trade name THERMOTRON-RF8 which was manufactured by YAMAMOTO VINITA CO., LTD. This high-frequency warming therapeutic device (THERMOTRON-RF8) can supply an electric power up to 1500 W, and it has been conventionally applied to treatment of cancer.

In the treatment procedure, the warming treatment by electric supply described above was performed for 60 minutes each time once a day everyday except for Sunday (6 times a week) over a period of the 1st and 2nd weeks after initiation of the therapy and then at an interval of 2 to 3 days (twice a week) over a period of the 3rd and 4th weeks. The watt numbers employed during the treatment period described above are shown in Table 1. The power supply described above was assumed to warm the patient's liver at 41 to 42° C.

TABLE 1

| | | | Case No. 1 (65-year male) | Case No. 2 (73-year male) | Case No. 3 (52-year female) | Case No. 4 (71-year female) | Case No. 5 (41-year female) |
|---|---|---|---|---|---|---|---|
| Output watt number upon warming treatment (W/h) | 1st week | 1st treatment | 650 | 1088 | 716 | 708 | 1094 |
| | | 2nd treatment | 943 | 1227 | 1091 | 792 | 1090 |
| | | 3rd treatment | 823 | 1256 | 1050 | 822 | 1000 |
| | | 4th treatment | 1107 | 1111 | 1069 | 500 | 922 |
| | | 5th treatment | 1118 | 1330 | 1071 | 856 | 1089 |
| | | 6th treatment | 1189 | 1217 | 1053 | 700 | 1082 |
| | 2nd week | 7th treatment | 1100 | 1100 | 1105 | 680 | 1105 |
| | | 8th treatment | 1100 | 1281 | 1108 | 908 | 1075 |
| | | 9th treatment | 1100 | 1200 | 1153 | 900 | 1083 |
| | | 10th treatment | 1100 | 1200 | 1157 | 790 | 815 |
| | | 11th treatment | 1216 | 1200 | 1143 | 679 | 1078 |
| | | 12th treatment | 1134 | 800 | 1160 | 714 | 1100 |
| | 3rd week | 13th treatment | 1192 | 1150 | 1123 | 700 | 1061 |
| | | 14th treatment | 1185 | 1148 | 1054 | 804 | 1115 |

TABLE 1-continued

|  |  | Case No. 1 (65-year male) | Case No. 2 (73-year male) | Case No. 3 (52-year female) | Case No. 4 (71-year female) | Case No. 5 (41-year female) |
| --- | --- | --- | --- | --- | --- | --- |
| 4th week | 15th treatment | 1134 | 1055 | 1135 | 611 | 996 |
|  | 16th treatment | 1063 | 1100 | 1159 | 696 | — |
|  | Mean | 1072 | 1154 | 1084 | 741 | 1047 |
| heating volume (cm$^3$) |  | 12717 | 15543 | 12717 | 14130 | 11304 |
| Output watt number per warmed volume (W/h/cm$^3$) |  | 0.084 | 0.074 | 0.085 | 0.052 | 0.092 |

During the 3rd and 4th weeks after initiation of the treatment, the warming treatment was combined with an interferon therapy. The interferon therapy was given as an intravenous injection once a day everyday except for Sunday (6 times a week).

In addition, the interferon therapy was given at the frequency of three times a week until the 15th week after initiation of the treatment in Case No.1, 14th week in Case No.2, 10th week in Case No.3 and 6th week in Case No.4. In the 5th week after initiation of the treatment and later, no warming treatment was given.

Blood samples were taken from peripheral vessels of Case Nos.1 to 5, and examined for the HCV RNA levels. The HCV RNA levels were determined 1 week, 2 weeks, 3 weeks and subsequent weeks after initiation of the treatment. The results are shown Table 2.

TABLE 2

| | | HCV RNA level (K copy) | | | | |
| --- | --- | --- | --- | --- | --- | --- |
| | | Case No. 1 (65-year male) | Case No. 2 (73-year male) | Case No.3 (52-year male) | Case No.4 (71-year male) | Case No.5 (41-year male) |
| Before treatment | | 2635.5 | 417.2 | 1605.6 | 5480.3 | 482.5 |
| After 1-week treatment | Warming | 3672.4 | 704.4 | 1817.1 | 3706.2 | 468.1 |
| After 2-week treatment | | 277.7 | 691.7 | 3990.6 | 2755.7 | 194.5 |
| After 3-week treatment | Warming + Interferon | 383.9 | 1192.2 | 33.0 | 2920.6 | — |
| After 4-week treatment | | 256.7 | 539.4 | 2.5 | 1901.0 | — |
| After 6-week treatment | Interferon | 25.9 | 360.2 | 1.3 | 959.2 | — |
| After 10-week treatment | | — | 582.4 | — | — | — |
| After 14-week treatment | | — | 282.4 | — | — | — |

As evident from Table 2, a marked reduction in the HCV RNA level was observed for example in Case Nos.1 and 3. Also in Case Nos.1, 4 and 5, the HCV RNA level was reduced substantially only by the warming treatment as is noted in the data of the 2nd week after initiation of the treatment. The results in Case No.4 was considered to be attributable to an insufficient warming of the liver due to the supplied power as low as 741 W on the average as is shown in Table 1. The results in Case No.2 was considered to be attributable to an insufficient warming of the liver due to the patient's body weight as heavy as about 80 kg in spite of the average supplied power as high as 1154 W.

Although the HCV RNA level was increased occasionally during a certain period after initiation of the treatment, it was reduced after the end of the treatment in any of Case Nos.1 to 5. Especially in view of the unsuccessful results of the interferon therapy over 2 therapeutic terms in Case Nos.1 to 4, the warming treatment of this invention is proven to be extremely effective.

Trial 2

Patients undergoing exacerbation from hepatitis C to hepatic cancer (Case Nos.6 to 10) were subjected to the warming treatment by supplying the electric power described above using a high-frequency warming therapeutic device (THERMOTRON-RF8 which was manufactured by YAMAMOTO VINITA CO., LTD.). In this warming treatment, the supplied electric power was about 1000 W/hr, and this power supply (warming treatment) was performed for 60 minutes each time once a day, everyday 8 times in total.

Figure 11:
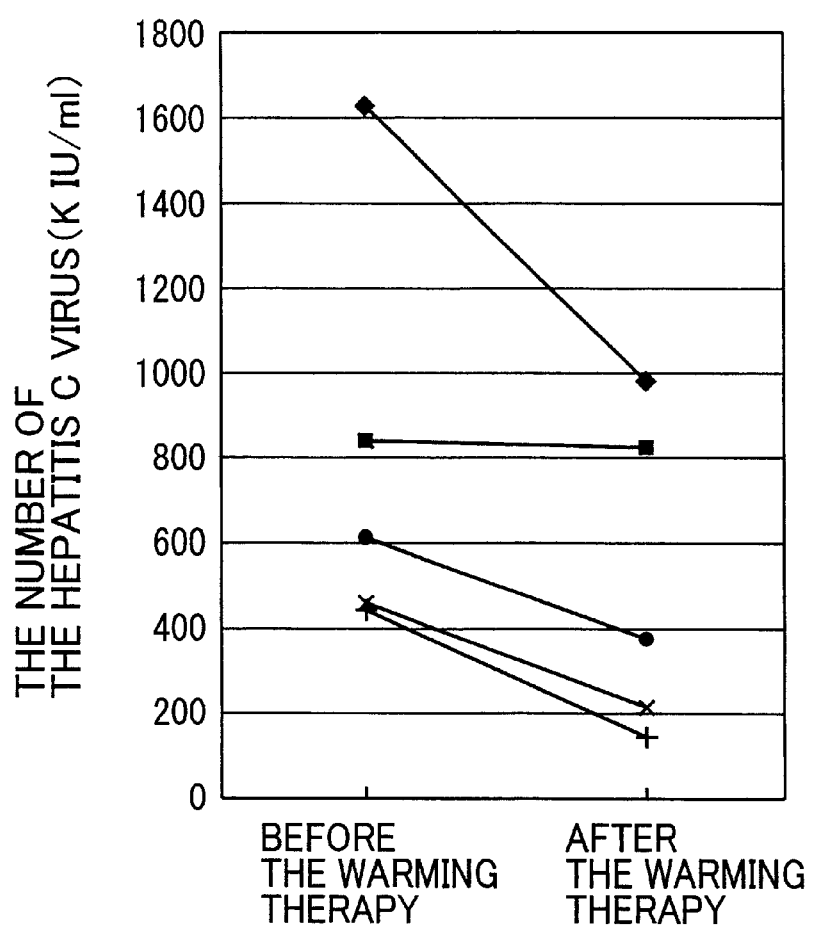
FIG. 11 shows the graph indicating the number of the Hepatitis C virus before and after the warming therapy.

Cases No.6 to 10 were examined for the hepatitis C virus counts before and after the warming treatment and the results are shown in FIG. 11.

As evident from FIG. 11, the warming treatment reduced the hepatitis C virus counts.

Experiment of Warming-induced Increase in Immunity

Experiment [1]

Mice were grouped into Group 1 and Group 2, and the trunk of each mouse in Group 1 (15 animals) was immersed in a water-bath at 42° C. for 30 minutes each time, once a day for consecutive 5 days, and the trunk of each mouse in Group 2 (15 animals) was immersed in a water-bath at 42° C. for 30 minutes each time, once a day every other day 5 times in total.

The mice in Group 1 and 2 were examined for the lymphocyte counts (Ly) and the white blood cell counts (WBC). The results are shown in FIGS. 8 and 9.

Figure 8:
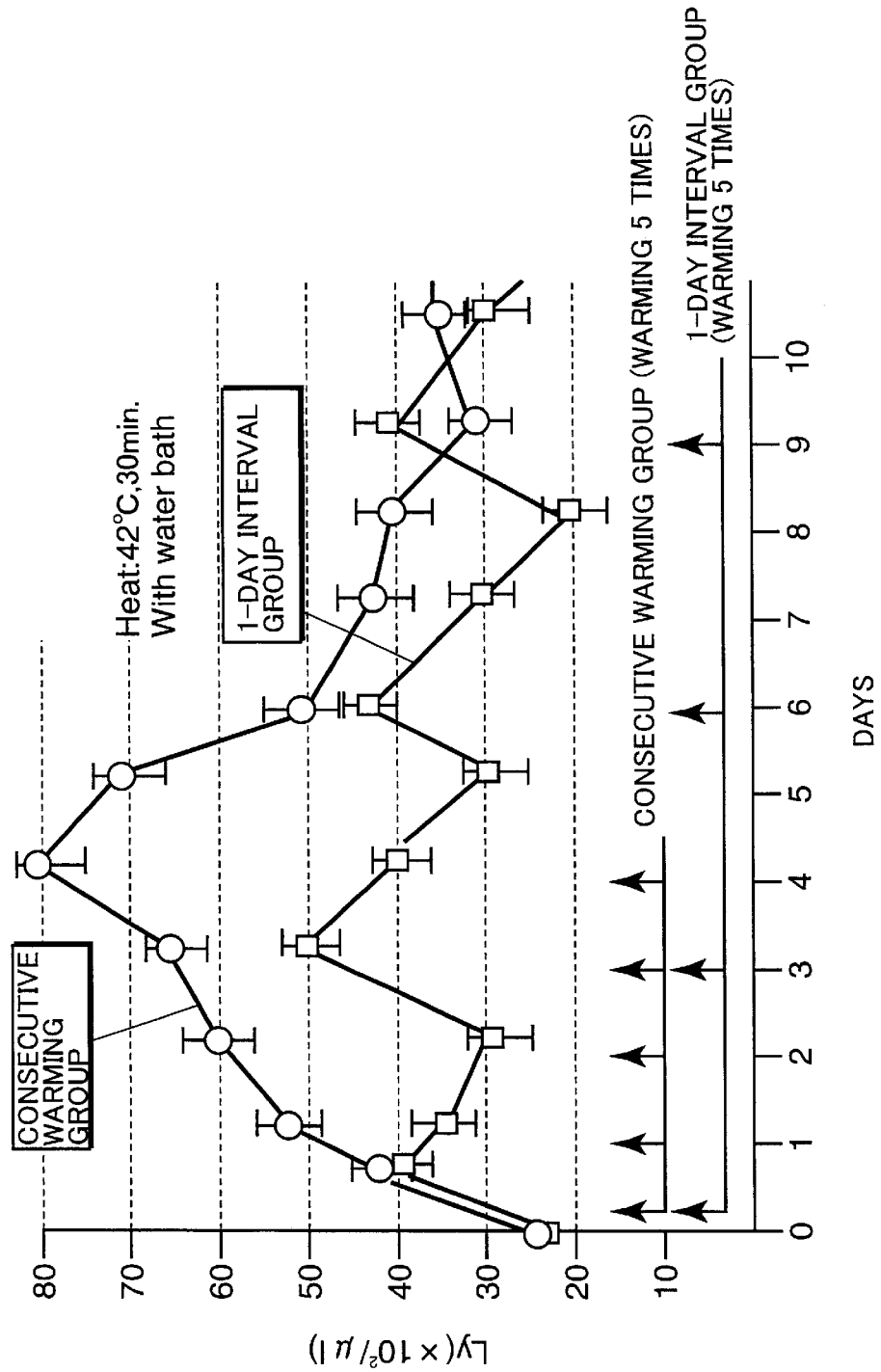
FIG. 8 shows the graph indicating the lymphocyte count (Ly) in mice after the warming therapy.
Figure 9:
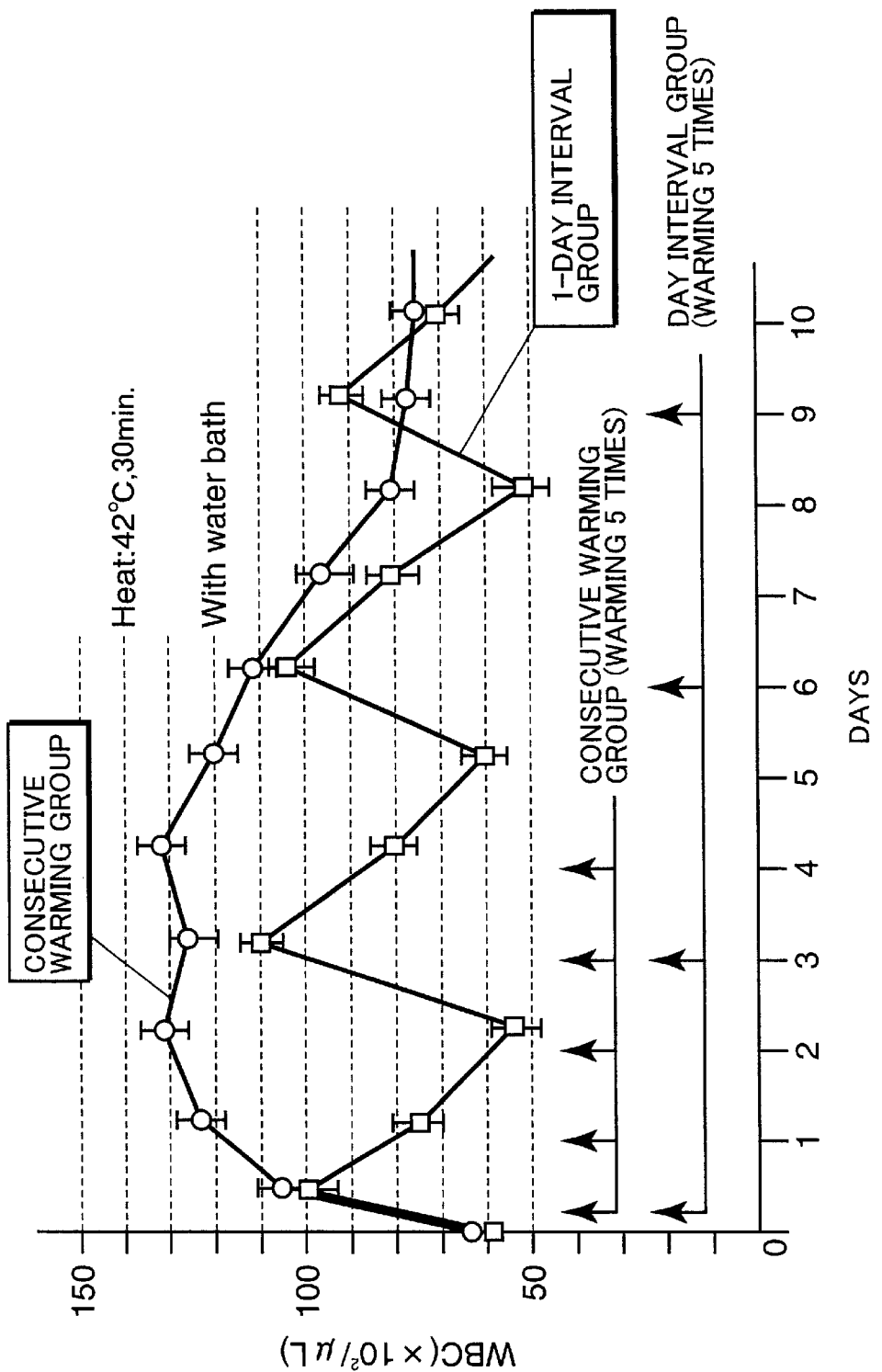
FIG. 9 shows the graph indicating the white blood cell count (WBC) in mice after the warming therapy.

As evident from FIGS. 8 and 9, the warming treatment increased the lymphocyte counts and the white blood cell counts, indicating an increased immune activity. It is also noted that the warming over consecutive days resulted in a higher immune activity as reflected by the further increases in the lymphocyte counts and the white blood cell counts in Group 1 receiving the warming over consecutive days rather than in Group 2 receiving the warming every other day.

Experiment [2]

Figure 10:
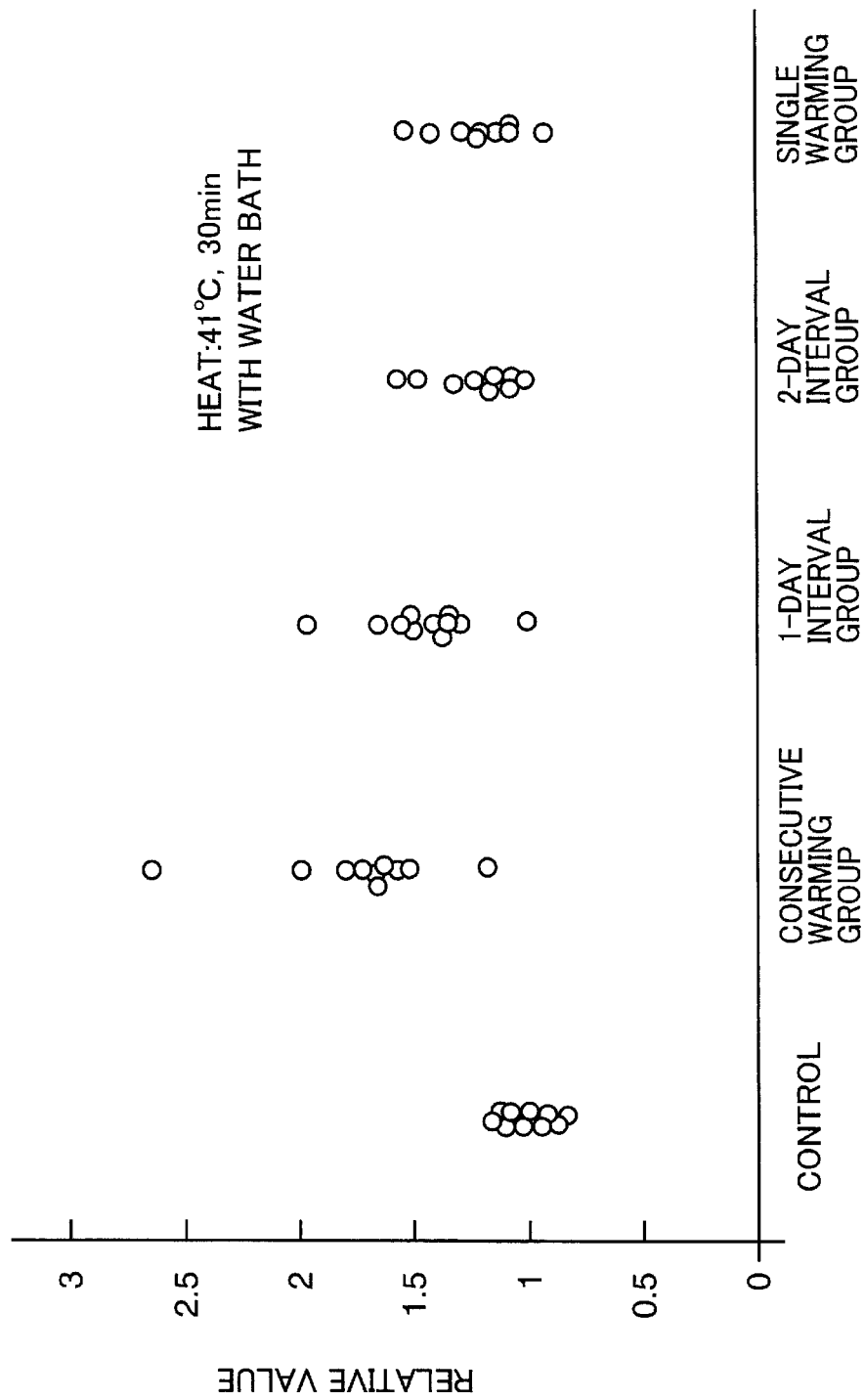
FIG. 10 shows the graph indicating the change in the NK cell activity subjected to the warming therapy in mice.

The trunk of each mouse was immersed in a water-bath at 41° C. for 30 minutes each time once a day everyday 5 times in total (consecutive warming group (10 animals)), once a day every other day 5 times in total (1-day interval group (10 animals)), once a day every third day 5 times in total (2-day interval group (10 animals)), only once (single warming group (10 animals)), and was not subjected to the warming with the water-bath described above (control group (10 animals)), and each mouse was examined for the activity of NK cell (natural killer cell). The results are shown in FIG. 10. In FIG. 10, the NK cell activity in each group is indicated as a relative value based on the mean value in the control group being regarded as 1.

As evident from FIG. 10, the NK cell activity was increased in mice receiving the warming, and a marked increase was observed especially in the group receiving the warming over consecutive days, indicating an increased immunity.

Based on the results of Experiments [1] and [2] described above, in the warming treatment by supplying an electric power given against hepatitis C described above, an increase in the immune activity due to the warming is assumed to contribute to the therapy of hepatitis C. It is also assumed that a further higher therapeutic effect is obtained by warming over consecutive days as possible rather than by any intermittent warming.

Experiment [3]

Healthy normal humans (Case Nos.11 to 14) were also subjected once to the warming treatment by supplying the electric power described above using a high-frequency warming therapeutic device (THERMOTRON-RF8 which was manufactured by YAMAMOTO VINITA CO., LTD.). In this warming treatment, the supplied electric power was about 1000 W/hr, which was given for 60 minutes.

Blood interferon levels were measured before and immediately after the warming treatment, and then after 1 hour, 2 hours, and subsequent hours. The results are shown in FIG. 12.

Figure 12:
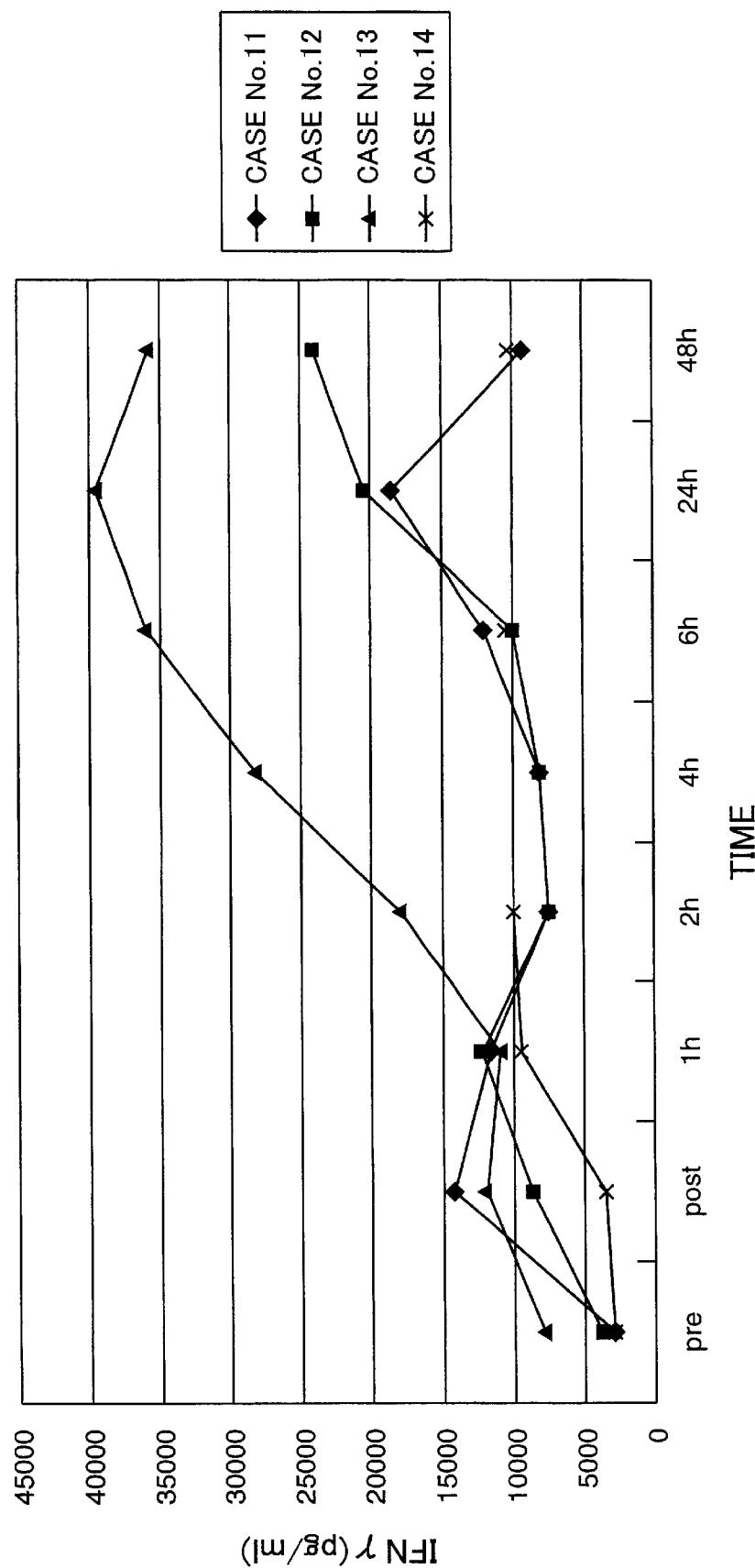
FIG. 12 shows the graph indicating the change of the amount of the interferon in blood by the warming therapy.

As evident from FIG. 12, an elevated interferon level was observed after the warming, suggesting that the warming served to enhance the interferon producing ability in each Case.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A method for treating hepatitis C comprising: a step of warming a liver region of a human body at 39 to 42° C. by supplying a high-frequency electric power, wherein said warming of the liver region is performed by sandwiching an upper abdominal region of a human body between electrodes on the front and back by supplying a high-frequency electric power.

2. A method for treating hepatitis C according to claim 1, wherein a high-frequency electric power of 200 to 1500 W is supplied to said electrodes.

3. A method for treating hepatitis C according to claim 1, wherein said electric power supply is performed 30 to 60 minutes each time.

4. A method for treating hepatitis C according to claim 1, wherein said electric power supply is performed once a week or more and 15 times or more in total.

5. A method for treating hepatitis C according to claim 1, wherein said electric power supply is performed once a day, three or more times for a week everyday or every other day and 15 times or more in total.

6. A method for treating hepatitis C according to claim 1, wherein said warming is performed while taking the systemic condition and the hepatitis C indices of a patient into consideration.

7. A method for treating hepatitis C according to claim 1, wherein an interferon is administered concomitantly while taking the systemic condition and the hepatitis C indices of a patient into consideration.

8. A method for treating hepatitis C according to claim 1, wherein the therapy is switched to an interferon therapy while taking the systemic condition and the hepatitis C indices of a patient into consideration.

9. A method for treating hepatitis C comprising: sandwiching the upper abdominal region of a human body between electrodes on the front and back by supplying a high-frequency electric power of 200 to 1500 W.

10. A method for treating hepatitis C according to claim 9, wherein said electric power supply is performed 30 to 60 minutes each time.

11. A method for treating hepatitis C according to claim 9, wherein said electric power supply is performed once a week or more and 15 times or more in total.

12. A method for treating hepatitis C according to claim 9, wherein said electric power supply is performed once a day, three times or more for a week everyday or every other day and 15 times or more in total.

13. A method for treating hepatitis C according to claim 9, wherein said electric power supply is performed while taking the systemic condition and the hepatitis C indices of a patient into consideration.

14. A method for treating hepatitis C according to claim 9, wherein an interferon is administered concomitantly while taking the systemic condition and the hepatitis C indices of a patient into consideration.

15. A method for treating hepatitis C according to claim 9, wherein the therapy is switched to an interferon therapy while taking the systemic condition and the hepatitis C indices of a patient into consideration.

16. A method for treating hepatitis C according to claim 9, wherein the impedance between said both electrodes is determined and said electric power is controlled when the impedance reached a predetermined percentage change.

* * * * *